United States Patent
Olalde Rangel (10) Patent No.: US 7,303,772 B2
(45) Date of Patent: Dec. 4, 2007

(54) SYNERGISTIC PHYTOCEUTICAL COMPOSITIONS

(76) Inventor: José Angel Olalde Rangel, Edificio Adaptogenos Internacionales, Calle del Arenal c/c Luis de Camoes, Baruta, Caracas (VE) 1080

( * ) Notice: Subject to any disclaimer, the term of this patent is extended or adjusted under 35 U.S.C. 154(b) by 0 days.

(21) Appl. No.: 11/271,940

(22) Filed: Nov. 10, 2005

(65) Prior Publication Data

US 2007/0104728 A1    May 10, 2007

(51) Int. Cl.
*A61K 36/00* (2006.01)

(52) U.S. Cl. .................................................. 424/728

(58) Field of Classification Search .................... None
See application file for complete search history.

(56) References Cited

U.S. PATENT DOCUMENTS

| | | | | |
|---|---|---|---|---|
| 6,129,924 | A * | 10/2000 | Maurel et al. | 424/400 |
| 6,264,994 | B1 * | 7/2001 | Castillo et al. | 424/725 |
| 6,541,045 | B1 * | 4/2003 | Charters et al. | 424/737 |
| 6,544,563 | B2 * | 4/2003 | Wuh et al. | 424/728 |
| 6,579,543 | B1 * | 6/2003 | McClung | 424/728 |
| 2004/0029955 | A1 * | 2/2004 | Kouge et al. | 514/459 |
| 2004/0147460 | A1 * | 7/2004 | Ramazanov et al. | 514/25 |
| 2004/0234544 | A1 * | 11/2004 | Jager et al. | 424/195.15 |
| 2005/0171034 | A1 * | 8/2005 | Halevie-Goldman | 514/28 |
| 2006/0035963 | A1 * | 2/2006 | Ashwell et al. | 514/454 |
| 2007/0041993 | A1 * | 2/2007 | Holcomb-Halstead et al. | 424/195.15 |

FOREIGN PATENT DOCUMENTS

CN    1511561 A    *    7/2004

OTHER PUBLICATIONS

Williams et al, Selected secondary metabolites from the phytolaccaceae and their biological pharmaceutical significance, Recent research developments in phytochemistry, vol. 6, 2002, pp. 13-68).*
Health Revolution (www.healthrevolution.co.za/herbs/sutherlandia.html).*
Olalde, Jose., "The Systemic Theory of Living Systems", Medicina Sistémica, www.adaptogeno.com, pp. 1-20 (2005).
Olalde Rangel., José A., "*The Systemic Theory of Living Systems and Relevance to CAM, Part I: The Theory*", Lecture Series, eCAM 2005:2(1)13-18.
Olalde Rangel., José A., "*The Systemic Theory of Living Systems and Relevance to CAM, The Theory Part II*", Lecture Series, eCAM 2005:2(2)129-137.
Olalde Rangel., José A., "*The Systemic Theory of Living Systems and Relevance to CAM, The Theory Part III*", Lecture Series, eCAM 2005:2(3)267-275.

* cited by examiner

*Primary Examiner*—Christopher R. Tate
*Assistant Examiner*—Deborah A. Davis
(74) *Attorney, Agent, or Firm*—Baker & McKenzie LLP (57) ABSTRACT

Phytoceutical compositions for the prevention and treatment of circulatory disorders, feminine endocrine disorders, and dermal disorders. A specific combination of extracts of plants is taught, as well as principles for varying the formulations based on categorizing plants into one of three groups, Energy, Bio-Intelligence, and Organization and selecting several plants from each group. Such combinations have synergistic effects, with minimal side effects.

2 Claims, 3 Drawing Sheets

Figure 1: Photographic evidence of Diabetic Foot remissions, including length of treatment between photos.

Doppler Ultrasound Toe

Figure 2: PCOS –before / after– echosonographic comparison. Interval between echosonograms: two months Figure 3: Photographic evidence of severe Psoriasis remissions, including length of treatment between photos

SYNERGISTIC PHYTOCEUTICAL COMPOSITIONS

PRIOR RELATED APPLICATIONS

Not applicable.

FEDERALLY SPONSORED RESEARCH STATEMENT

Not applicable.

REFERENCE TO MICROFICHE APPENDIX

Not applicable.

FIELD OF THE INVENTION

The invention relates to phytoceutical formulations used to treat a variety of diseases. The formulations are particular combinations of plants and have synergistic effect in combination. Principles for selecting beneficial formulations are provided.

BACKGROUND OF THE INVENTION

The academic study of medicinal plants for the treatment of diverse diseases has been nearly as pervasive as the study of Western medicines—The active principles from many traditional medicines have been extracted from plants, the curative agents identified and their mechanisms of action determined. Plant based medicines are typically well tolerated, with less severe side effects as well as a smaller range of side effects. However, despite the excellent medicinal qualities of many plants, they are individually insufficient to take chronic degenerative diseases into remission. In contrast, while synthetic drugs can be highly effective, their use is often hampered by severe side effects. What is needed in the art are better treatment regimes with improved patient tolerance, while providing sufficient efficacy.

SUMMARY OF THE INVENTION

A number of known beneficial plants were classified according to their capacity to enhance the three main elements that support overall health: Energy (E), Bio-intelligence (I) and Organization (O). A synergistic effect is expected when all three categories of herbs (E, I, O) are included in a formulation, preferably at least two or three or four plants from each catagory. Thus, one embodiment of the invention provides a method of selecting additional disease treating formulations according to these principles. Three examples of formulations prepared in this way are provided and additonal formulations are being prepared and tested.

Another embodiment of the invention provides an effective, natural composition for treating circulatory diseases. The composition can be used alone, or can be combined with simultaneous use of one or more pharmaceutical compositions. It can be used for the treatment of diabetic lesions, obliterative arteriosclerosis, Leriche syndrome (aorto-iliac obliteration), Buerger's disease (thromboangiitis obliterans), thrombophlebitis, chronic venous insufficiency, varicose veins, varicose ulcers, hemorrhoids, and the like.

Another embodiment of the invention provides a composition for the treatment of feminine endocrine diseases that can be used alone or combined with pharmaceuticals. It provides an effective medicine for diseases such as Polycystic Ovary Syndrome, ovarian cysts, fibrocystic breast condition, uterine fibroids, dysfunctional uterine hemorrhage, female infertility, premenstrual syndrome, amenorrhea, and the like.

Another embodiment of the invention provides a composition for chronic skin disorders. It can be used alone or combined with pharmaceuticals, and can be used to treat diseases such as psoriasis, dermatitis, skin infections, shingles (herpes zoster), boils, eczema, rash, acne or burn, and the like.

DETAILED DESCRIPTION OF THE FIGURES

DETAILED DESCRIPTION OF THE INVENTION

Figure 1:
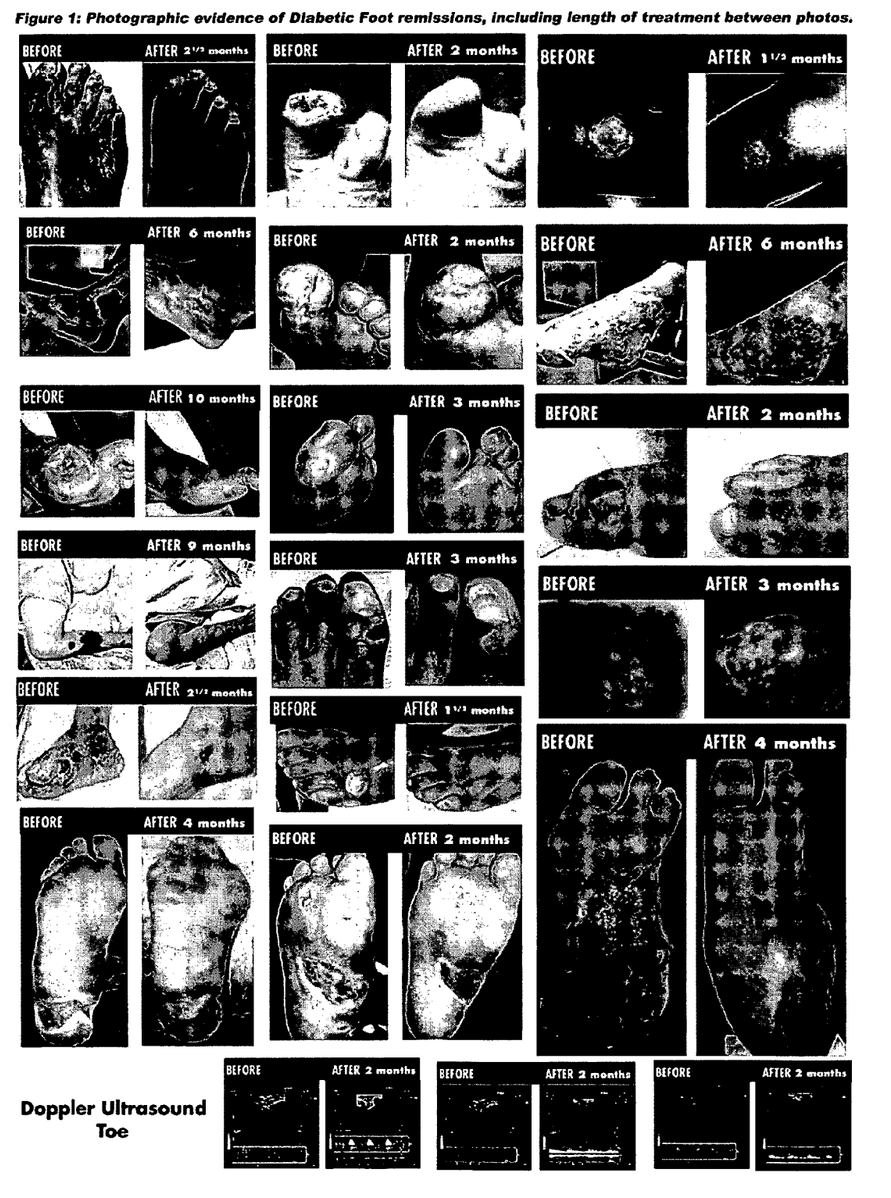
FIG. 1 shows representative examples of diabetic foot lesions treated with the herbaria of Table 1.
Figure 2:
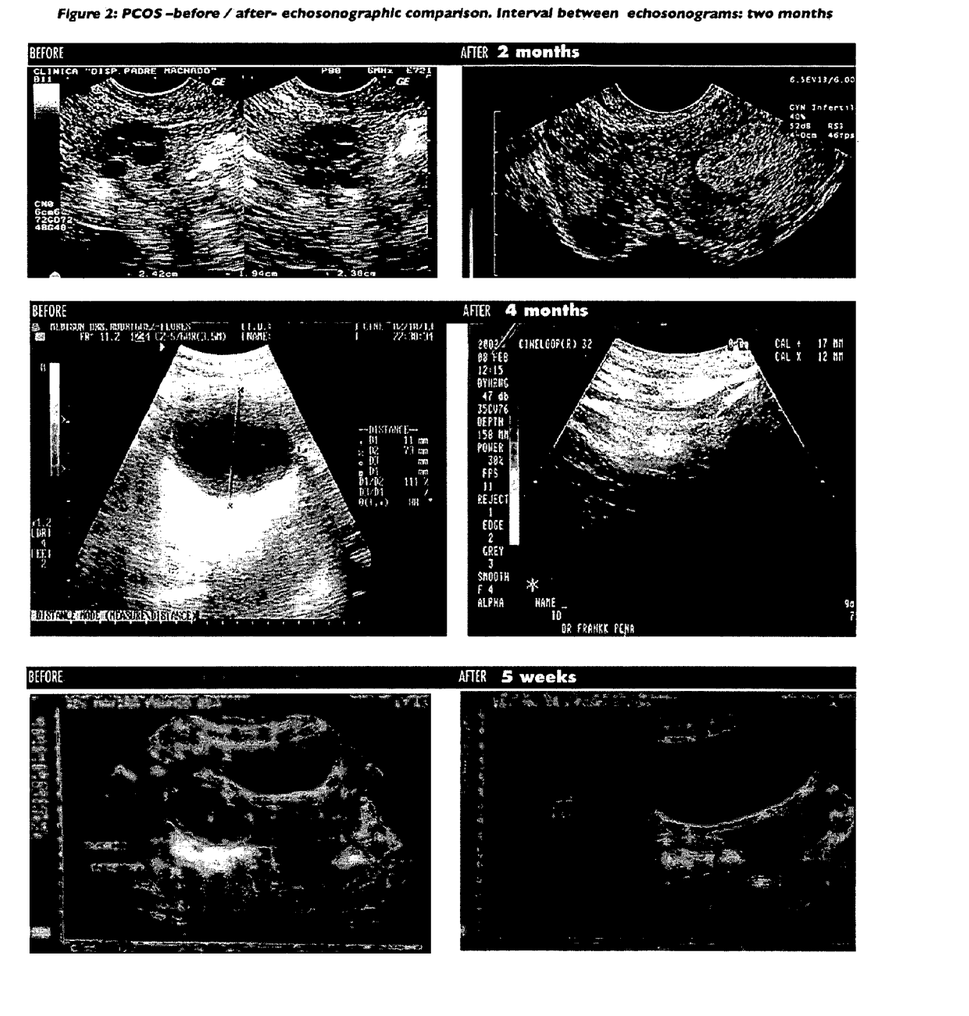
FIG. 2 shows representative examples of PCOS treated with the herbaria of Table 2.
Figure 3:
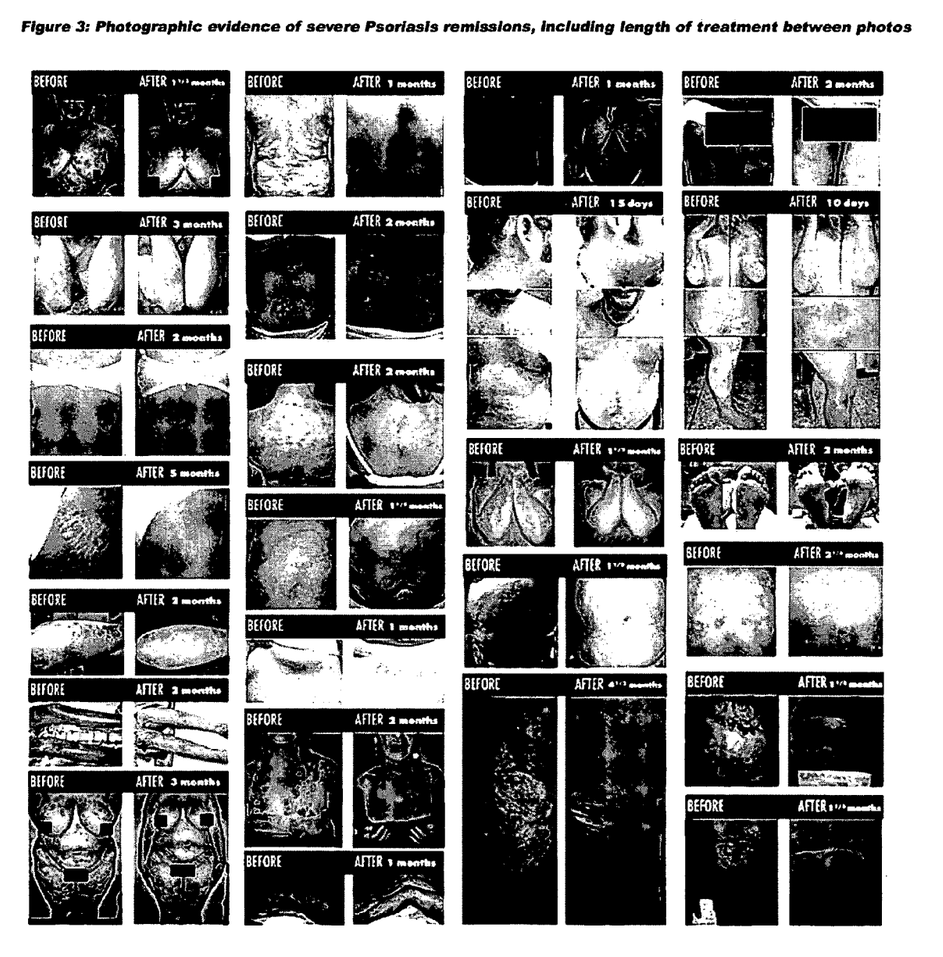
FIG. 3 shows representative examples of psoriasis treated with the herbaria of Table 3.

"Pharmaceutically acceptable excipients" is used herein according to art accepted meanings, and includes those ingredients needed to formulate a medicine for mammalian use, including the use of gelatin capsules.

"Synergistic" or "synergy" is used herein to mean that the effect is more than its additive property. In preferred embodiments, the synergy is at least 1.5, 2, 5, or 10 fold.

By use of "plants," what is meant herein is that the plant (or that portion with medicinal activity) is used whole, ground, or as an extract. Also included are purified active ingredients and derivatives thereof. However, it is believed that the best efficacy of plants used herein is achieved with the use of the entire plant or its extracts, rather than with the use of isolated active ingredients.

Further, although plants are named here according to commonly used nomenclature, with improving taxonomy plants are often reclassified. Whenever a plant is referenced, it includes related species with similar active ingredients.

The following examples are illustrative only and should not serve to unduly limit the invention.

EXAMPLE 1

Plant Characteristics—Circulatory Disorders

*Angelica sinensis* (Dong Quai or *Angelica*, also *Angelica Archangelia, Angelica Pubescens* and *Angelica Sylvestris*) contains terpenes (terpenes, mainly β-phellandrene, with β-bisabolene, β-caryophyllene, β-phellandrene, α- and β-pinene, limonene, linalool, borneol, acetaldehyde, menthadienes, and nitromenthadienes), macrocyclic lactones (including tridecanolide, 12-methyl tridecanolide, pentadecanolide), phthalates (such as hexamethylphthalate), coumarins (especially furocoumarin glycosides such as marmesin and apterin), angelicin and byakangelicin derivatives (osthol, umbelliferone, psoralen, bergapten, imperatoren, xanthotoxol, xanthotoxin, oxypeucedanin and more), as well as various sugars, plant acids, flavonoids, and sterols.

*Acanthopanax senticosus* (Russian *Ginseng*, Siberian *Ginseng*, Eleuthero, Devil's Shrub, Touch-me-not, Wild Pepper, Shigoka, *Acantopanacis senticosus*) contains terpenoids (oleanolic acid), glycosides (Eleutheroside A (daucosterin), B1, C-G, I, K, L, M), phytosterols (β-sitosterol), coumarins (Eleutheroside B1 and B3, isofraxidine), polysaccharides (eleutherans), volatile oils, caffeic acid, coniferyl aldehyde, and sugars. Eleuthero has been shown to bind to estrogen, progestin, and mineralocorticoid receptors, and stimulate T-lymphocyte and natural killer cell production. It has activity anti-platelet aggregation activity similar to aspirin, as well as antioxidant activity. Russian *Ginseng* contains at least 40 active ingredients.

*Rhaponticum carthamoides* (Leuzea, or Maral Root) contains a mixture of compounds called, "levseins." Levseins represents a complex of more than 10 ecdysterones including 20-beta-ecdysterone, makisterone C, 24-dehydromakisterone A, carthamosterone, polypodyne B and ajugasterone C. Researchers extracted and purified various ecdysteroids from *Rhaponticum* and found that the ecdysteroids increased the mass of the developing quails in a dose-dependent manner, with the rate of increase proportional to the ecdysteroids content. The Soviets manufactured a synthetic version of this powerful substance for their athletes with great success. Soon after, the U.S. version called Mesobolin circulated on the underground market for a long time. Incorporation of this phytomedicine in a composition provides at least 10 active principles in a single therapeutic.

*Panax ginseng* (Chinese *ginseng*, *panax*, ren shen, jintsam, ninjin, Asiatic *ginseng*, Japanese *ginseng*, Oriental *ginseng*, Korean red *ginseng*) main active components are ginsenosides (Ra1, Ra2, Rb1, Rg1, Rd, Re, Rh1, Rh2, Rh3, F1, F2, F3) and panoxosides, which have been shown to have a variety of beneficial effects, including anti-inflammatory, antioxidant, and anticancer effects. Results of clinical research studies demonstrate that *Panax ginseng* may improve psychological function, immune function, and conditions associated with diabetes. Studies indicate that *Panax ginseng* enhances phagocytosis, natural killer cell activity, and the production of interferon; improves physical and mental performance in mice and rats; causes vasodilation; increases resistance to exogenous stress factors; and affects hypoglycemic activity. It stimulates hepatic glutathione peroxidase, and the phytosterols inhibit prostaglandin synthesis. Also it displays vascular activity because the saponins act like calcium antagonists in the vasculature. The incorporation of this phytomedicine provides at least 86 active principles in a single therapeutic.

*Panax quinquefolius* (American *Ginseng*, Anchi, Canadian *Ginseng*, Five Fingers, *Ginseng*, American, North American *Ginseng*, Red Berry, Ren Shen, Tienchi) is related to *Panax ginseng*, but is a distinct species with higher levels of ginsenoside Rb1 and without ginsenoside Rf. Ginsenoside Rb1 is believed to limit or prevent the growth of new blood vessels, making it useful to treat tumors. Research suggests that several of *ginseng*'s active ingredients also have a beneficial influence on platelet aggregation. It also demonstrates an anti-atherosclerotic action, apparently mediated by a correction in the imbalance between prostacyclin and thromboxane. Other studies that have found panaxynol or the lipophilic fraction to be the most potent anti-platelet agent in *ginseng*, chiefly due to an inhibition of thromboxane formation. This possibly occurs via regulation of cGMP and cAMP levels and prolongation of the time interval between the conversion of fibrinogen to fibrin. Ginsenosides have also been shown to be relatively potent platelet activating factor antagonists. It has antioxidant, anti-inflammatory, and hypolipidemic effects. The incorporation of this phytomedicine into a composition provides at least 206 active principles in a single therapeutic.

*Pfaffia paniculata* (Suma, Brazilian *Ginseng*, *Pfaffia*, Para Toda, Corango-acu; also *Hebanthe paniculata*, *Gomphrena paniculata*, *G. eriantha*, *Iresine erianthos*, *I. paniculata*, *I. tenuis*, *P. eriantha*, *Xeraea paniculata*) contains active glycosides (beta-ecdysone and three ecdysteroids), pfaffic acids, phytosterols (sitosterol and estimasterol). It also contains saponins. Its germanium content probably accounts for its properties as an oxygenator at the cellular level, and its high iron content may account for its traditional use for anemia. This herb increases oxygenation at the cellular level, and it also has anabolic activity at the muscular and cardiac levels by improving the contraction of the miocardia and diminishing arrhythmias and stabilizing the membranes of cardiac cells. The incorporation of this phytomedicine provides 44 active principles in a single therapeutic.

*Rhodiola rosea* (Golden Root, Roseroot) consists mainly of phenylpropanoids (rosavin, rosin, rosarin (specific to *R. rosea*), phenylethanol derivatives (salidroside, rhodioloside, tyrosol), flavanoids (catechins, proanthocyanidins, rodiolin, rodionin, rodiosin, acetylrodalgin, tricin), monoterpenes (rosiridol, rosaridin), triterpenes (daucosterol, beta-sitosterol), and phenolic acids (chlorogenic and hydroxycinnamic, gallic acids). It also contains organic acids (gallic, caffeic, and chlorogenic acids) and p-Tyrosol. There are many species of *Rhodiola*, but it appears that the rosavins are unique to *R. Rosea*, and it is the preferred species. Its therapeutic properties include a strong estrogen binding property. It also has properties of vasodilatation by activation of mu-opiate receptors in heart muscle, and it is a hypolipidemic, diminishing cholesterol and triglyceride levels. The incorporation of this phytomedicine provides at least 20 active principles in a single therapeutic.

*Echinacea angustifolia* or *purpurea* (Black Sampson, Purple Coneflower, Rudbeckia, Missouri Snakeroot, Red Sunflower) contains alkaloids (Isotussilagine, tussilagine), amides (echinacein, isobutylamides), carbohydrates (echinacin, polysaccharides (heteroxylan and arabinogalactan), inulin, fructose, glucose, pentose), glycosides (echinacoside), terpenoids (Germacrane), Cichoric acid, betaine, methyl-para-hydroxycinnamate, vanillin, phytosterols, and volatile oils. *Echinacea* has been the subject of hundreds of clinical and scientific studies which have primarily used an extract of the root and aerial portions of the botanical. The rich content of polysaccharides and phytosterols in *Echinacea* are what make it a strong immune system stimulant. The sesquiterpene esters also have immuno-stimulatory effects. *Echinacea* has also been found to possess anti-fungal and antibiotic properties. This component of *Echinacea* also has cortisone-like actions which can help promote the healing of wounds and helps to control the inflammatory reactions. The incorporation of this phytomedicine into compositions provides at least 70 active principles in a single therapeutic.

*Ganoderma lucidum* (Reishi, also *G. tsugae*, *G. valesiacum*, *G. oregonense*, *G. resinaceum*, *G. pfezfferi*, *G. oerstedli*, and *G. ahmadii*) is an edible fungus containing bitter triterpenoids (ganoderic acid), β-D-glucan, coumarins, alkaloids and ergosterols. It has vasodilator effect and is useful in the treatment of angina. It is hypolipidemic and anti-arthrotic. It contains at least 32 active principles.

*Grifola frondosa* (Maitake, Dancing Mushroom; also *G. sordulenta*, *Polyporus umbellatus* and *Meripilus giganteus*) contains the primary polysaccharide, β-D-glucan in the 1.3 and 1.6 forms. It also contains alpha glucan, lipids, phospholipids, and ergosterol. Animal studies suggest maitake may lower serum cholesterol and triglycerides. Beta-D-glucan is also recognized as an effective immuno-stimulator. This substance increases the activity of macrophages and other immunocompetent cells that destroy tumor cells. The substance also improves the immunological efficiency of these cells by increasing production of cytokines IL-1, IL-2 and lymphokines. The final result is an increase of the defenses against infectious diseases. The incorporation of this phytomedicine provides at least 6 active ingredients for therapeutic use.

*Hydrastis canadensis* (golden seal, yellow root, turmeric root) contains mainly isoquinoline alkaloids (xanthopuccine, berberine, hidrastine, hidrastanine, beta-hydrastine, canadine and canadaline). These confer anti-inflammatory, bacteriostatic, bacteriocidal, and vasodilator effects. In general, its antibacterial action is directed to metabolic inhibition, inhibition of the formation of enterotoxins, and inhibition of bacterial adhesion. It produces vasodilatation by inhibiting smooth muscle contraction, and inhibiting platelet aggregation. This plant provides at least 34 active principles for therapeutic use.

*Petiveria alliacea* (Anamú, Apacin, Apacina, Apazote De Zorro, Aposin, Ave, Aveterinaryte, Calauchin, Chasser Vermine, Congo Root, Douvant-douvant, Emeruaiuma, Garlic Guinea Henweed, Guine, Guine, Guinea, Guinea hen leaf, Gully Root, Herbe Aux Poules, Hierba De Las Gallinitas, Huevo De Gato, Kojo Root, Kuan, Kudjuruk, Lemtewei, Lemuru, Mal Pouri, Mapurit, Mapurite, Mucura-caa, Mucura, Mucuracaa, Ocano, Payche, Pipi, Tipi, Verbena Hedionda, Verveine Puante, Zorrillo) contains Allantoin, Arborinol, Arborinoliso Astilbin, Benzaldehyde, Benzoic-acid Benzyl-2-hydroxy-5-ethyl-trisulfide, Coumarin, Dibenzyl Trisulfide, Engeletin, alpha Friedelinol, Isoarborinol, Isoarborinol-acetate, Isoarborinol-cinnamate, Isothiocyanates, Kno3, Leridal, Leridol, Leridol-5-methyl Ether, Lignoceric Acid, Lignoceryl Alcohol, Lignoceryl Lignocerate, Linoleic Acid Myricitrin, Nonadecanoic Acid, Oleic Acid, Palmitic Acid, Pinitol, Polyphenols, Proline, trans-n-methyl-4-methoxy, Senfol, β-Sitosterol, Stearic Acid, Tannins, and Trithiolaniacine. Its therapeutic activities include anti-inflammatory, immune-stimulant and antimicrobial effects. This phytomedicine provides about 25 active principles.

*Sutherlandia frutescens* (Cancer Bush, also *Sutherlandia Microphylla*) contains L-canavanine, pinitol, GABA (gamma aminobuteric acid), and asparagine. In addition, novel triterpenoid glucoside known as "SU1" has been isolated and characterized. The therapeutic indications include anti-inflammatory, antioxidant, immuno-modulador, and vasodilator effects. This phytomedicine provide at least 5 active principles.

*Tabebuia avellanedae* (Pau d'arco, *Ipê*, Lapacho, Tahuari, Taheebo, Trumpet Tree, *Tabebuia Ipê*, Tajy; also *T. ipe, T. nicaraguensis, T. schunkeuigoi, T. serratifolia, T. altissima, T. palmeri, T. impetiginosa, T. heptaphylla, Gelseminum avellanedae, Handroanthus avellanedae, H. impetiginosus, Tecoma adenophylla, Tec. avellanedae, Tec. eximia, Tec. impetiginosa, Tec. integra, Tec. ipe*) extracts contain diverse quinone derivatives and a small quantity of benzenoids and flavonoids, including beta-lapachone, xyloidone, tabebuin, quercetin, tecomine, and steroidal saponins. One important ingredient is lapachol, a derivative of which was patented in 1975. It has anti-inflammatory and antibacterial effects. The incorporation of this phytomedicine into a composition provides at least 32 active principles in a single therapeutic.

*Uncaria tomentosa* (Cat's Claw, Peruvian Cat's Claw, Samento, Saventaro, Uña de Gato, also *Uncaria guianensis*) has several alkaloids including pentacyclic oxindole alkaloids (POA) (isomitraphylline, isopteropodine, mitraphylline, pteropodine, speciophylline, uncarine F), tetracyclic oxindole alkaloids (TOA) (isorynchophylline, rynchophylline), glycosides (triterpenic quinovic acid glycosides), hirsutine, tannins, catechins, phytosterols (beta-sitosterol, campesterol, stigmasterol), triterpenes, polyphenols, flavanols and oligomeric proanthocyanidins (OPC). It is an immune-stimulant, an anti-inflammatory, vasodilator, and antioxidant. In laboratory testing, rynchophylline displays an ability to inhibit platelet aggregation and thrombosis, suggesting that cat's claw may be useful in preventing strokes and reducing the risk of heart attack by lowering blood pressure, increasing circulation, inhibiting formation of plaque on arterial walls and formation of blood clots in the brain, heart and arteries. This phytomedicine provides at least 10 active ingredients.

*Petiveria Alliacea* (Anamú, Apacin, Apacina, Apazote De Zorro, Aposin, Ave, Aveterinaryte, Calauchin, Chasser Vermine, Congo Root, Douvant-douvant, Emeruaiuma, Garlic Guinea Henweed, Guine, Guine, Guinea, Guinea hen leaf, Gully Root, Herbe Aux Poules, Hierba De Las Gallinitas, Huevo De Gato, Kojo Root, Kuan, Kudjuruk, Lemtewei, Lemuru, Mal Pouri, Mapurit, Mapurite, Mucura-caa, Mucura, Mucuracaa, Ocano, Payche, Pipi, Tipi, Verbena Hedionda, Verveine Puante, Zorrillo) contains Allantoin, Arborinol, Arborinoliso Astilbin, Benzaldehyde, Benzoic-acid Benzyl-2-hydroxy-5-ethyl-trisulfide, Coumarin, Dibenzyl Trisulfide, Engeletin, alpha Friedelinol, Isoarborinol, Isoarborinol-acetate, Isoarborinol-cinnamate, Isothiocyanates, Kno3, Leridal, Leridol, Leridol-5-methyl Ether, Lignoceric Acid, Lignoceryl Alcohol, Lignoceryl Lignocerate, Linoleic Acid Myricitrin, Nonadecanoic Acid, Oleic Acid, Palmitic Acid, Pinitol, Polyphenols, Proline, trans-n-methyl-4-methoxy, Senfol, β-Sitosterol, Stearic Acid, Tannins, and Trithiolaniacine. Its therapeutic activities includes anti-inflammatory, immuno-stimulant and antimicrobial. This phytomedicine provides about 25 active principles.

*Angelica sinensis* (Dong quai or *Angelica*, also *Angelica archangelia, Angelica pubescens* and *Angelica sylvestris*) contains terpenes (terpenes, mainly β-phellandrene, with β-bisabolene, β-caryophyllene, β-phellandrene, α- and β-pinene, limonene, linalool, borneol, acetaldehyde, menthadienes and nitromenthadienes), macrocyclic lactones (including tridecanolide, 12-methyl tridecanolide, pentadecanolide), phthalates (such as hexamethylphthalate), coumarins (especially furocoumarin glycosides such as marmesin and apterin), angelicin and byakangelicin derivatives (osthol, umbelliferone, psoralen, bergapten, imperatoren, xanthotoxol, xanthotoxin, oxypeucedanin and more), as well as various sugars, plant acids, flavonoids, and sterols. These components have vasodilator activity, increase coronary flow and are antithrombotic. The incorporation of this phytomedicine into compositions provides at least 70 active principles in a single therapeutic.

*Crataegus oxyacantha* (Hawthorn, see also *C. monogyna*) contains mainly flavonoids (such as flavonoglycosyls, hyperoside, rutin, flavonol, kaempferol, quercetin) and oligomeric procyanadins (1-epicatechol), which relax arterial expansion to decrease peripheral vascular resistance. Also contains amines (phenyletylamine, tyramine, O-methoxyphenethylamine), flavone (apigenin, luteolin) derivatives, vitexin glycosides, tannins, saponins, and cyanogenetic glycosides. The incorporation of this phytomedicine into a composition provides at least 52 active principles in a single therapeutic plant.

*Croton lechleri* (Dragon's blood, Sangre de Grado, Sangre de Agua; also *C. draconoides, C. palanostigma, C. erythrochilus C. salutaris*, and *C. gossypifolius*) produces a distinctive red exudate from its trunk containing a considerable amount of secondary plant metabolites, the majority of which are hydrolyzing flavonoids, proanthocyanidins (mainly catechin, epicatechin, gallocatechin and/or galloepicatechin), as well as taspine. Other components include the dihydrobenzofuran lignan, six simple phenols and their derivatives, three steroids, non-saturated fatty acids, diterpenoids (hardwickiic acid, bincatriol, crolechinol, crolechinic acid, coberine A, coberine B), and diterpenoids. It heals wounds and ulcers of vascular origin. Incorporation of this phytomedicine into a composition provides at least 23 active principles in a single therapeutic.

*Ginkgo biloba* (*Ginkgo*) contains ginkgolides, bilobalides, bioflavones and flavone glycosides. Flavone glycosides include quercetin, 3-methylquercetin and kaempferol. Quercetin, myrcetin and the rest of the flavonoid fraction of the extract have antioxidant and free radical scavenger effects. The flavonoids diminish infiltration by neutrophils and increase blood flow. Their antioxidant properties and membrane stabilizing activity increase the tolerance to hypoxia. They improve cellular metabolism and protect against the damage caused by ischemia. Ginkgolide B is a powerful inhibitor of platelet activating factor (PAF), binding to its membrane receptors, and antagonizing platelet aggregation. Similarly, it has anti-inflammatory effect by decreasing vascular permeability, and has vasodilator activity by inhibiting the liberation of thromboxane B2 and prostaglandins. Controlled double blind clinical studies conclusively demonstrate the effectiveness of *Gingko biloba* in treating peripheral arterial insufficiency. The incorporation of this phytomedicine into a composition provides at least 59 active principles in a single therapeutic.

*Hydrocotyle asiatica* (Gotu Kola, Bramhi, Pennywort, Marsh Penny, Pennywort; also *Hydrocotile asiatica asiatica*) contain terpenoids (triterpenes, asiaticoside, brahmoside and brahminosidea, (saponin glycosides) aglycones, asiaticentoic acid, centellic acid, centoic acid and madecassic acid), sesquiterpenes (caryophyllene, trans-B-farnesene), volatile oils (Germacrene D), alkaloids (hydrocotylin), flavones (Quercetin, kaempferol, sesquiterpenes, stigmasterol, and sitosterol), and vallerine, fatty acids, resin, and tannins. It is used to treat chronic venous insufficiency, varicose veins, and venous hypertension. Incorporation of this phytomedicine in a composition provides at least 59 active principles in a single therapeutic.

*Ruscus aculeatus* (Butcher's Broom, Box Holly, Jew's Myrtle, Knee Holly, Kneeholm, Pettigree, Sweet Broom) contains as primary active ingredients the steroidal saponins (ruscogenin and neoruscogenin), but other constituents have been isolated, including flavonoids, tetracosanoic acid, chrysophanic acid, sitosterol, campesterol, stigmasterol, triterpenes, coumarins, sparteine, tyramine, and glycolic acid. Its ingredients reduce vascular permeability, have anti-elastic properties and are vasoconstrictors. The incorporation of this phytomedicine in a composition provides at least 28 active agents.

*Vaccinium myrtillus* (European blueberry or bilberry, closely related to American blueberry, cranberry, and huckleberry) contains anthocyanosides such as: cianadins, malvidins, petunidins and peonidins. Other ingredients include arbutin, asperuloside, astragalin, beta-amyrin, caffeic-acid, catechin, chlorogenic-acid, cyanadin-3-O-arabinoside, dihydroxycinnamic-acid, epicatechin, epigallocatechin, epimyrtine, ferulic-acid, gallic-acid, gallocatechin, hydroquinone, hyperoside, isoquercitrin, lutein, coumaric-acids, m-hydroxybenzoic-acid, monotropein, myrtillin, myrtillol, myrtine, neomyrtillin, protocatechuic-acid, quercetins, quinic-acid, resinic-acid, syringic-acid, ursolic-acid, and vanillic-acid. Evidence suggests that anthocyanosides may benefit the retina, as well as strengthen the walls of blood vessels, reduce inflammation, and stabilize collagen containing tissues. The anthocyanosides improve the activity of enzymes lactic dehydrogenase, glucose-6-phosphatase and phosphoglucomutase, each involved in processes of vascular damage. They reduce the arterial deposits and stimulate the production of vasodilators, like prostaglandin (PG12), thus protecting the vascular wall. Anthocyanosides have strong antioxidant properties, as well. The incorporation of this phytomedicine into a composition provides at least 63 active principles in a single therapeutic.

EXAMPLE 2

Composition—Circulatory Disorders

A particularly preferred composition is shown in Table 1. Ratios reflect the concentration of active ingredient over the natural state, and the amounts provided are mg of extract. Obviously, the amount should be increased where the strength is reduced, and vice versa.

TABLE 1

Herbaria

| Active Agent | Ratio | Amount (mg) |
|---|---|---|
| Energy enhancers | | |
| *Eleutherococcus senticosus* root extract | 5:1 | 53.53 |
| *Rhaponticum carthamoides* root extract | 12:1 | 3.85 |
| *Panax ginseng* root extract | 5:1 | 10.71 |
| *Panax quinquefolius* root extract | 5:1 | 32.12 |
| *Pfaffia paniculada* (Suma) root extract | 4:1 | 21.41 |
| *Rhodiola rosea* root extract | 5:1 | 9.64 |
| Bio-Intelligence modulators | | |
| *Echinacea angustifolia* root extract | 6:1 | 1.34 |
| *Echinacea purpurea* root extract | 6:1 | 1.34 |
| *Ganoderma lucidum* extract | 6:1 | 32.12 |
| *Grifola frondosa* extract | 10:1 | 12.85 |
| *Hydrastis canadensis* root extract | 5:1 | 38.54 |
| *Petiveria alliacea* | 1:1 | 64.24 |
| *Sutherlandia frutescens* | 1:1 | 64.24 |
| *Tabebuia avellanedae* bark extract | 4:1 | 40.15 |
| *Uncaria tomentosa* root extract | 10:1 | 16.06 |
| Organization improvers | | |
| *Angelica sinensis* root extract | 5:1 | 64.24 |
| *Crataegus oxyacantha* fruit extract | 5:1 | 42.83 |
| *Croton lechleri* bark resin extract | 10:1 | 10.71 |
| *Ginkgo biloba* leaf extract | 50:1 | 19.49 |
| *Hydrocotyle asiatica* plant extract | 5:1 | 64.24 |
| *Ruscus aculeatus* root extract | 5:1 | 57.82 |
| *Vaccinium myrtillus* fruit extract | 5:1 | 38.54 |
| Total | | 700 mg |

EXAMPLE 3

Plant Characteristics—Female Endocrine Disorders

*Panax quinquefolius* The active principles responsible for its therapeutic effects are triterpensaponides, of which more than 25 different types have been identified. These are denominated protopanaxadiols (ginsenosides Rc, Rd, Rb1, Rb2) and protopanaxatriols (ginsenosides –Re, –Rf, –Rg 1, etc.). Panax also contains hydrosoluble polysaccharides (panaxans A-U) and polyacetylenes (ginsenosides A-K, panaxynol and panaxatriol). These substances confer energizing properties because they increase ATP synthesis. On the other hand they reduce the secretion of prolactin by increasing dopaminergic activity or by activating dopamine receptors at the anterior hipophysis level. Prolactin is a hormone involved in the appearance of anovulatory cycles and dysfunctional uterine hemorrhages, menorrhea, mammary fibrocystic condition, and cyclic mastalgy. The reduction of this hormone explains the recovery in the treatment of uterine dysfunctional hemorrhages, Polycystic Ovary Syndrome (PCOS), Ovary Cysts, fibromyomatous uteri, and infertility.

*Pfaffia paniculata* Its most important active principles are: Beta-ecdysone and three glycoside ecdysteroids, six different pfaffic acids, phytosterols and nortriterpenic glycosides. These substances are energizing through an increase in ATP synthesis and oxygenation at the cellular level. Also, its phytosterols act as hormone originators, and have demonstrated effectiveness in the management of diverse conditions associated with hormone imbalance, such as: premenstrual syndrome, dysmenorrhea, infertility, dysfunctional uterine hemorrhages, and menopause.

*Rhodiola rosea* See above.

*Astragalus membranaceus* (Huang-Qi) This plant contains three main types of active principles. Isoflavones, which act as anti-oxidants; astragalans which act as immune-stimulants and anti-inflammatory by stimulating the phagocytic activity of macrophages, of the cytotoxic response of T and NK lymphocytes and of the production and activity of interferon; and astragalans which act as modulators of the hypothalamus-hypofisis-adrenal axis response.

*Echinacea* See above.

*Dioscorea villosa* (Rheumatism root, huesos del dialo, Yuma, Yam, Wild Yam, Chinese Yam, Mexican Yam, raiz china, and colic root) contains steroid sapogenins (dioscine, dioscorin and diosgenine) as the main active principles. Diosgenine can change into ecdysone, pregnenolone, and progesterone, thus, diosgenine is a hormonal precursor, which contributes to the neuroendocrine system's modulation. On the other hand, diosgenine has demonstrated its important pro-apoptotic effects, in the therapy of benign and malign tumors, including mammary and ovarian cysts, and uterine fibroids.

*Ganoderma lucidum* and *Grifola frondosa* The main active principles of these mushrooms are sterols and beta-proteoglucans which bestow anti-inflammatory and immune-modulating properties, because they increase the phagocytotic capacity of macrophages and increase the production and lifespan of CD4 lymphocytes.

*Tabebuia avellanedae* contains diverse substances derived from quinones, such as Alfa and Beta lapachone [2-hidroxi-3-(3-metil-2-butenil)-1,4-naftoquinona] and cyclopentane dialdehydes. These confer important anti-inflammatory, pro-apoptotic, antimitotic and cytostatic effects, in treating benign and malign tumors including mammary and ovarian cysts as well as uterine fibroids.

*Uncaria tomentosa* See above.

*Vitex agnus castus* (Chaste Tree or chaste berry) An essential oil is extracted from the fruit of this plant, two iridoid glycosides (aucubine and agnuside); a flavone (casticine, which seems to be the primary active principle) and 3 minor flavonoids derived from kaempferol and quercetin. These active principles act on the anterior hypofisis dopaminergic-D2 receptors, modulating prolactin secretion. This hormone is implicated in the appearance of anovulatory cycles and dysfunctional uterine hemorrhages, menorrhea, mammary fibrocystic condition, and cyclic mastalgy. *Vitex agnus castus* modulates the secretion of LH from the hypofisis, which act on the ovary, starting up the luteal phase and progesterone secretion. Therefore, *Vitex* benefits dysfunctional uterine hemorrhages, premenstrual syndrome, PCOS, infertility, ovary cysts, menopause, and fibromyomatous uteri.

*Hydrocotile asiatica* See above. Also, the active principles include pentacyclic triterpene saponins. The major active principles are asiaticosides and madecassosides. Other minor saponins are the centelloside, brahmosides, brahminosides and *Hydrocotile asiatica* saponins B, C and D. Mucopolysaccharides are the core components of the cellular matrix. The biochemical action of these active principles reduce the levels of lysosomal enzymes associated with the degradation of mucopolysaccharides. On the other hand, the active agents act on the fibroblasts of the connective tissue, modulating collagen synthesis and inhibiting inflammatory processes. This diminishes the fibrosis processes important to fibrocystic mammary and uterine conditions.

EXAMPLE 4

Composition—Female Endocrine Disorders

A particularly preferred composition is shown in Table 2.

TABLE 2

Herbaria II

| Active Agent | Ratio | Amount (mg) |
|---|---|---|
| Energy enhancers | | |
| *Rhodiola rosea* root extract | 5:1 | 8.16 |
| *Panax quinquefolius* root extract | 4:1 | 67.97 |
| *Pfaffia paniculada* (Suma) | 4:1 | 54.37 |
| Bio-Intelligence modulators | | |
| *Astragalus membrenaceus* root extract | 5:1 | 73.41 |
| *Echinacea angustifolia* | 6:1 | 20.39 |
| *Echinacea angustifolia* radix | 6:1 | 3.40 |
| *Echinacea purpurea* | 6:1 | 20.39 |
| *Echinacea purpurea* radix | 6:1 | 3.40 |
| *Dioscorea villosa* | 4:1 | 125.74 |
| *Ganoderma lucidum* extract | 6:1 | 36.25 |
| *Grifola frondosa* mushroom extract | 10:1 | 21.75 |
| *Tabebuia avellanedae* | 4:1 | 67.97 |
| *Uncaria tomentosa* | 10:1 | 24.47 |
| *Vitex agnus castus* | 5:1 | 57.09 |
| Organization improvers | | |
| *Hydrocotile asiatica asiatica* | 5:1 | 65.25 |
| Total | | 650 |

EXAMPLE 5

Plant Characteristics—Dermal Disorders

*Lepidium meyenii* (Maca) Its major active principles are: alkaloids (Macaridina, Lepidiline A and B); benzyl-isotiocyanate and glucosinolates; macamides; Beta-ecdysone and phytosterols. These substances activate ATP synthesis which confers energizing properties.

*Rhaponticum carthamoides* See above.

*Panax ginseng* The active principles responsible for its therapeutic effects are triterpensaponides of which more than 25 different types have been identified. These include protopanaxadiols (ginsenosides Rc, Rd, Rb1, Rb2) and protopanaxatriols (ginsenosides –Re, –Rf, –Rg 1, etc.).

Panax also contains hydrosoluble polysaccharides (panaxans A-U) and polyacetylenes (ginsenosides A-K, panaxynol and panaxatriol). These substances confer energizing properties because they increase ATP synthesis.

*Rhodiola rosea* See above. Also, the active principles in this plant (phenylpropanoids, phenylethanol derivatives, flavonoids, monoterpenes and phenolic acids) activate the synthesis of ATP in mitochondria and stimulate reparative energy processes.

*Andrographis paniculata* (King of Bitters, Chirettta, Kalmegh and Kiryat) Primary active principles associated with *Andrographis* are: flavonoids, glucosides and diterpenic lactones (andrographolides). These substances offer immuno-modulator and anti-inflammatory properties. Even though their precise mechanism of action is not known, studies suggest that they stimulate the immune systems and activate macrophages.

*Angelica sinensis* contains alkyl phthalides (Ligustilide); terpenes, phenylpropanoids (ferulic acid) and benzenoids. These substances stimulate the immune system's actions, through diverse lymphokines and have an anti-inflammatory effect by inhibiting 5-lipoxygenase and elastase, as well as selectively inhibiting 12-(S)-HHTrE production, a marker of cyclo-oxygenase activity.

*Astragalus membranaceus* See above. Also, *Astragalus membranaceus* inhibits 5-lipoxygenase and elastase, which indicates that it is valuable in the management of skin pathologies involving chronic inflammation, such as psoriasis.

*Echinacea* See above.

*Hydrastis canadensis* The most important active principles of *Hydrastis* are isoquinoline alcaloides (Berberina, hydrastina, Hidrastanina, Canadina, Canadalina) which award anti-inflammatory, and immuno-modulating properties. Berberine inhibits activating protein 1 (AP-1), a key factor in transcription the inflammation. It also exerts a significant inhibitory effect on lymphocyte transformation, so its anti-inflammatory action seems to be due to the inhibition of DNA synthesis in the activated lymphocytes or to the inhibition of the liberation of arachidonic acid from the phospholipids of the cellular membrane. It also has immuno-modulating properties by increasing the production of immunoglobulins G and M and stimulating the phagocytotic capacity of macrophages.

*Ganoderma lucidum* The main active principles of this mushroom are sterols and beta-proteoglucans that bestow anti-inflammatory and immune-modulating properties by increasing the phagocytotic capacity of macrophages and raising production and lifespan of CD4 lymphocytes.

*Uncaria tomentosa* see above.

*Equisetum arvense* (Horse tail) This plant contains abundant mineral salts particularly silicic acids and silicates. It also contains phytosterols, phenolic acids, flavonoids (mainly quercetin glycosides and apigenine) and saponins (equisetonin). These active principles block the liberation of arachidonic acid, which diminishes inflammation and reduces the proliferation of keratinocytes, as well as inducing G2/M arrest in keratinocytes. The action mechanism is in part due to the inhibition of mitotic kinase activity of p34cd2 and perturbation of cyclin B1 levels.

*Hydrocotile asiatica* See above.

*Tabebuia avellanedae* contains diverse quinone derivatives such as alpha and beta-lapachone, cyclopentane dialdehydes and a small quantity of benzenoids and flavonoids, including, xyloidone, tabebuin, quercetin, tecomine, and steroidal saponins. These compounds inhibit keratinocyte growth and offer anti-inflammatory and antibacterial effects, which are of great importance in the treatment of psoriasis.

*Shilajit* (*Mumiyo*) *Mumiyo* is a natural complex substance, whose active principles are carboxylic acids: (hydroxylated derivatives of Benzoic, Phenylacetic and Hippuric acids), fulvic and humic acids, minerals and amino acids. Of *Mumiyo*'s known properties, the most important ones are its ability to reduce excessive inflammatory reactions and stimulate tissue regeneration. Oral intake of *Mumiyo* has been used to treat burns, trophic non-healing wounds, eczema, and other skin diseases, such as psoriasis. It has been established that fulvic/humic acids stimulate respiration and oxidative phosphorylation in liver mitochondria, increase mechanical resistance of collagen fibers, activate human leucocytes, reduce excessive inflammatory reactions, and stimulate tissue regeneration.

Shark cartilage This natural compound reduces psoriatic plaque vascularization. It inhibits the proliferation of endothelial cells, competitively blocking the Endothelial Growth Factor at the receptor level. It also inhibits tyrosine EGF and EGF-2 dependant phosphorylation as well as the increase of FCE induced permeability. Shark cartilage also induces endothelial cell apoptosis, by inducing caspase 3, 8 and 9 activation, and the liberation of cytochrome c from the mitochondria to the cytoplasm. Shark cartilage also induces fibrinolitic activity by increasing the secretion, activity and affinity of Tissue Plasminogen Activator (tPA) for endothelial cells. It also inhibits extracellular matrix degradation, by inhibiting matrix metalloproteinases MMP-2, MMP-7, MMP-9, MMP-12 and MMP-13. It also stimulates production of angiostatin.

*Schizandra chinensis* The major active principles of *Schizandra* (also known as Wuweizi and Wurenchum) are lignans called schizandrines. These substances have known hepato-protective and hepato-regenerative properties. It maintains the integrity of hepatocyte cellular membranes; increases hepatic levels of ascorbic acid; inhibits NADPH oxidation; inhibits lipid peroxidation at the hepatic microsomal level as well as formation of hepatic malondialdehyde; diminishes production of carbon monoxide at the hepatic level; has an inductor effect in the enzymatic anti-toxic microsomal hepatic cytochrome P-450; increases biliary flow and the excretion of toxic substances; promotes recovery of hepatic functions; induces mRNA formation for the Hepatocyte Growth Factor (HGF); encourages the proliferation of the hepatocyte's endoplasmic smooth reticula, and accelerates the proliferation of hepatocytes; increases omithine decarboxylase activity as well as the mitotic index, facilitates DNA synthesis and hepatic proteins; increases levels of glutathione, glutathione reductase and glucose-6-phosphate, improving the regeneration capacity of the liver.

*Silybum marianum* (Milk Thistle) The active principles of this plant are flavonolignans, including silibine, silicristine and silidianine and isosilibinin collectively known as sylimarin. This compound has the highest grade of hepato-protective, hepato-generating, and anti-inflammatory activity. The mechanisms which explain its hepato-protector characteristics are diverse and include anti-oxidation, lipid anti-peroxidation, detoxification increase through a competitive inhibition with toxic substances, as well as protection against the depletion of glutathione. One of the mechanisms that can explain its hepato-regenerative properties is the increase in protein synthesis, obtained thanks to a significant boost in the formation of ribosomes, DNA synthesis and proteins at the hepatic level, because the active principles join a specific polymerase receptor, stimulating ribosome formation. Its anti-inflammatory effect is due to the stabilization of the mastocytes, the inhibition of neutrophils, a strong inhibition of leucotriene (LT) synthesis and formation of prostaglandins. Sylimarin inhibits intestinal beta-glucuronidase enzymes, thus improving glucoronization, which is an important step in hepatic detoxification. More corporal toxins are removed via glucoronization than through other detox pathways.

*Picrorhiza kurroa* The most important active constituents are iridoid glycoside picrosides I, II, III and kutkoside, known collectively as kutkin. Though less well researched than *Silybum*, it appears to have similar applications and mechanisms of action. When compared with *Silybum*, the curative efficacy of *Picrorhiza* was found to be similar, or in many cases superior, to the effect of *Silybum*. *Picrorrhiza* possesses significant antioxidant activity, by reducing lipid peroxidation and free radical damage. Like sylimarin, it has also an effect on liver regeneration. *Picrorrhiza* also offers anti-inflammatory effects, inhibiting the infiltration of pro-inflammatory cells. One of its minor components, apocynin exhibits powerful anti-inflammatory effects, without affecting beneficial activities such as phagocytosis, chemotaxis or humoral immunity.

*Smilax* spp. (sarsaparilla) Its main active principles are: phytosterols, Steroid Saponins, Phenolic acids, Flavonoids and minerals. These substances adhere to toxins inside the gastrointestinal tract, this way reducing their absorption by the circulatory stream. On the other hand it improves the hepatic and renal excretory functions, facilitating the removal of toxic substances and waste found in cells, blood vessels and lymphatic system. Also, phytosterols block prostaglandin synthetase action, explaining its anti-inflammatory action and use to treat psoriasis.

*Vaccinium myrtillus* Angiogenesis appears to be a fundamental inflammatory response early in the pathogenesis of psoriasis and significant abnormalities of vascular morphology and vascular endothelial growth factor (VEGF) play a crucial role in the vascularization of psoriatic plaques. During inflammatory skin diseases such as psoriasis, the skin initiates angiogenesis through VEGF and the active principles of this plant (anthocyanosides, flavonoids, quercetin, tannins, iridoids and phenolic acids) significantly inhibit VEGF expression by the human keratinocytes, reducing the psoriatic plaque's angiogenesis.

EXAMPLE 6

Composition—Dermal Disorders

A particularly preferred composition is shown in Table 3.

TABLE 3

| Herbaria | | |
|---|---|---|
| Active Agent | Ratio | Amount (mg) |
| Energy enhancers | | |
| *Rhaponticum carthamoides* root extract | 6:1 | 0.72 |
| *Rhodiola rosea* root extract | 5:1 | 9.66 |
| *Szchisandra chinensis* | 5:1 | 16.10 |
| Bio-Intelligence modulators | | |
| *Angelica sinensis* | 5:1 | 32.20 |
| *Astragalus membranaceus* root extract | 5:1 | 48.30 |
| *Echinacea angustifolia* | 6:1 | 8.05 |
| *Echinacea angustifolia* radix | 6:1 | 1.34 |
| *Echinacea purpurea* | 6:1 | 8.05 |
| *Echinacea purpurea* radix | 5:1 | 1.61 |

TABLE 3-continued

| Herbaria | | |
|---|---|---|
| Active Agent | Ratio | Amount (mg) |
| *Ganoderma lucidum* mushroom extract | 6:1 | 35.78 |
| *Hydrastis canadensis* | 5:1 | 19.32 |
| *Lepidium meyenii* | 5:1 | 48.30 |
| *Panax ginseng* root extract | 5:1 | 16.10 |
| *Silibum marianum* | 5:1 | 28.98 |
| Shark Cartilage extract | 4:1 | 93.92 |
| *Tabebuia avellanedae* | 4:1 | 67.08 |
| *Uncaria tomentosa* | 10:1 | 14.49 |
| Organization enhancers | | |
| *Equisetum arvense* | 5:1 | 22.54 |
| Fulvic Acid -Shilajit 65% | 1:1 | 13.95 |
| *Hydrocotile asiatica* | 5:1 | 42.94 |
| *Picrorhiza kurroa* (Standardized 4% Kutkin) | 5:1 | 32.20 |
| *Smilax officinialis* | 5:1 | 72.45 |
| *Vaccinium mirtyllus* | 5:1 | 16.10 |
| Total | | 650 |

EXAMPLE 7

Tolerance Studies

A multicentric, retrospective study was made on 100 healthy volunteers with the intention of evaluating patient tolerance and side effects of the herbaria combination. A capsule containing 700 mg of the herbaria of Table 1 was administered to each participant three times per day for five days. During that period they were evaluated by a physician, who registered any finding or symptom reported by each subject. The average age of the participants was 37.4 years with a SD of 8.2 years. Gender was 55% female, 45% male. The average weight of the subjects was 70 kilos with a SD of 12.3 kilos. No undesirable effects were observed in 96% of the subjects. Four (4%) subjects reported minor undesirable effects.

The study showed that herbaria were well tolerated—only minor symptoms were reported by 4 of the 100 subjects. These results showed the non-toxicity of the herbaria, demonstrating that the formulation is safe. Similar results have been obtained for the PCOS and Psoriasis formulations.

EXAMPLE 8

Clinical Studies

To evaluate the efficacy of the combination, 110 patients affected with diverse degrees of lesions of the diabetic foot, were studied by means of retrospective, multicentric, and descriptive study for two year duration. Of these patients, 50 had grade III-V lesions, and were diagnosed for surgical amputation of the affected area. The patients were treated as above, with ten 700 mg capsule of herbaria three times a day, but the treatment was continued on an as needed basis for times ranging from 1.5 months to 10 months. The data is summarized in Table 4.

TABLE 4

Diabetic Foot Lesion Study

| Number of Patients | Clinical Improvement | QoL* Improvement | Treatment tolerance | Other |
|---|---|---|---|---|
| 110 | 80.9% (89 patients) | 86.4% (95 patients) | 97.3% (107 patients) | Amputation avoided in 80% of the cases diagnosed for surgery |

*QoL is Quality of Life

It is significant to note that the herbaria treatment prevented amputation in 40 patients (80% of the population) who were already diagnosed for surgical removal of portions of the foot. In contrast, in the usual course of standard medical treatment, almost 100% of these patients could have expected to have a partial or complete amputation. Thus, these superior results are quite unexpected and clearly demonstrate the novel and non-obvious qualities of the formulation.

Likewise, 129 patients with chronic varicose ulcers were evaluated. The treatment (six 700 mg capsules three times a day) improved ulcers in 79% of the population, and remission was achieved in 21% of the population in only two months (Table 5). The systemic treatment also significantly improved the most frequent symptoms (cramps 71.4%, pain 78%, and edema 88.7%). In contrast, most patients with chronic varicose ulcers do not achieve remission under existing pharmaceutical treatments and have high risk of amputation.

TABLE 5

Chronic Varicose Ulcer Study

| Number of Patients | Clinical Improvement | QoL Improvement | Treatment tolerance | Remission time |
|---|---|---|---|---|
| 129 | 79% (102 patients) | 81.2% (105 patients) | 99.2% (128 patients) | 2 months in 21% of all patients |

In a study of 35 patients with Polycystic Ovary syndrome (PCOS), the treatment improved pelvic pain in all 20 symptomatic patients, menstrual disorder (amenorrhea, dysmenorrhea, menometrorrhea, oligomenorrhea) in all 22 symptomatic patients, asthenia and cephalea in all 17 symptomatic patients, as well as acne and hirsutism in 8 of 9 symptomatic patients. Pelvic echo sonograms revealed that 29 patients (82.9%) experienced a total disappearance of cysts, while another 6 (17.2%) showed a decrease in cyst size. In contrast, most patients with PCOS do not achieve symptomatic relief without surgical intervention, and very few, if any, have a complete disappearance of cysts (Table 6). The dosage was six 650 mg capsules three times a day.

TABLE 6

Polycystic Ovary Syndrome Study

| Number of Patients | Clinical Improvement | Cyst Disappearance | QoL Improvement | Treatment tolerance |
|---|---|---|---|---|
| 35 | 100% | 82.9% (29 patients) | 100% | 100% |

Similarly, in a study of 123 patients with severe psoriasis, clinical remission was observed in 77% of the patients, and almost two thirds of the patients achieved clinical improvement in less than 45 days (Table 7). In contrast, most patients with severe psoriasis do not achieve remission, but only symptomatic relief with existing pharmaceutical approaches. The dosage was seven 650 mg capsules three times a day.

TABLE 7

Severe Psoriasis Study

| Number of Patients | Clinical Improvement | QoL Improvement | Treatment tolerance | Remission time $\leq$45 days |
|---|---|---|---|---|
| 123 | 77.2% (95 patients) | 66.3% | 100% | 82.9% (102 patients) |

In conclusion, these results indicate that synergistic combinations of phytoceuticals, scientifically chosen from each category of herbal tonics described in the next section, is suprisingly effective!

EXAMPLE 9

Principles for Selecting Synergistic Combinations

In order to expand the range of formulations encompassed by the invention, we have categorized beneficial plants into one of three groups, each of which should be present for synergistic effect. The classifications are Energy, Bio-Intelligence and Organization. Plants classified under Energy are associated with ATP synthesis (such as the Krebs cycle, oxidative phosphorylation, beta-oxidation, etc.). Plants classified under Bio-Intelligence are those that regulate the neuroendocrine and immunological systems and cellular processes, thus controlling the interactions between the various systems in the body. Finally, plants classified under Organization are those that relate to the structure and function of specific organs. Combinations of plants from these three classification groups have synergistic effect because they address each necessary component of cellular and organic health—in effect they provide the triangle on which healing is fully supported.

A large group of plants were classified (along with some vitamins, etc.) according to this system, based on what is known in the literature about their active ingredients and mode of action. The classification is presented in Table 8. Table 8 is representative only: based on the criterion described herein, additional plants can easily be categorized as their mode of action is elucidated.

TABLE 8

Plant Categories

| Energy | Bio-Intelligence | Organization |
|---|---|---|
| *Acantopanacis senticosus* | *Agaricus blazei* | *Angelica sinensis* |
| *Ajuga turkestanica* | *Aloe vera* | *Buplerum chinense* |
| *Codonopsis pilosula* | *Andrographis paniculata* | *Cimicifuga racemosa* |
| *Cordyceps sinensis* | *Annona muricata* | Chitin fiber |
| *Cornu Cervi pantotrichum* | *Aralia mandschurica* | Chondroitin sulphate |
| *Ilex paraguariensis* | *Astragalus membranaceus* | *Crataegus oxyacantha* |
| L-arginine | Beta 1.3 glucan | *Croton lechleri* |
| *Lepidium meyenii* | Beta 1.6 glucan | *Curcubita pepo* |
| *Ocimum sanctum* | *Camelia sinensis* | *Curcuma longa* |

TABLE 8-continued

Plant Categories

| Energy | Bio-Intelligence | Organization |
|---|---|---|
| Panax ginseng | Coriolus versicolor | Dioscorea villosa |
| Panax quinquefolius | Echinacea angustifolia | Equisetum arvense |
| Pfaffia paniculata | Echinacea purpurea | Eucommia bark |
| Ptychopetalum olacoides | Ganoderma lucidum | Fructus ligustri lucidum |
| Rhaponticum carthamoides | Grifola frondosa | Fructus lycii |
| Rhodiola rosea | Hydrastis Canadensis | Fulvic acid |
| Schizandra chinensis | Lactoferrin | Gentiana lutea |
| Ubiquinone (Coenzime Q10) | Lentinus edodes | Ginkgo biloba |
| | Lobostomon trigonus | Glucosamine |
| | Morinda citrifolia | Glycyrrhiza glabra |
| | Petiveria alliacea | Gynostemma |
| | Polygonum multiflorum radix | Harpagophytum procumbens |
| | Radix apeoniae alba | Herba epimedii |
| | Radix polygalae | Hydrocotile asiatica |
| | Shark cartilage | Linum usitatissimum |
| | Sutherlandia frutescens | Minerals |
| | Tabebuia avellanedae | Mumiyo |
| | Turnera aphrodisiaca | Opuntia ficus indica |
| | Uncaria tomentosa | Picrorhiza kurroa |
| | Valeriana officinalis | Plants enzymes |
| | Vitex agnus castus | Ptycopetalum olacoides |
| | | Pygeum africanum |
| | | Rhamnus purshiana |
| | | Ruscus aculeatus |
| | | Salix alba |
| | | Sargassum fusiforme |
| | | Sena alejandrina |
| | | Serenoa repens |
| | | Silibum marianum |
| | | Smilax china |
| | | Solamun nigrum |
| | | Tribulus terrestris |
| | | Ulmus fulva |
| | | Urtica dioica |
| | | Uva ursi |
| | | Vaccinium myrthillus |
| | | Viburnum spp |
| | | Vitamins |

An illustrative example of synergy in medicinal plants is an in vitro study that demonstrates how the activity of herbal Berberine alkaloids is strongly potentiated by the action of herbal 5'-methoxyhydnocarpin (5'-MHC). It shows a strong increase of accumulation of berberine in the cells in the presence of 5'-MHC, indicating that this plant compound effectively disabled the bacterial resistance mechanism against the berberine antimicrobial, thus showing the synergy of both substances. Stermitz F R, et al., Synergy in a medicinal plant: antimicrobial action of berberine potentiated by 5'-methoxyhydnocarpin, a multidrug pump inhibitor. Proc Natl Acad Sci USA. Feb 15, 2000; 97(4):1433-7.

We expect to further demonstrate synergistic effect on a molecular scale by studying the gene expression profile changes in response to various plant ingredients and combinations thereof. Experiments are already underway demonstrating the expression profile in response to the formulations. We will be aided in this work because researchers have already begun studying the expression profiles of various medicinal plants, thus providing a database of knowledge from which to build. E. g., Gohil, et al., mRNA Expression Profile of a Human Cancer Cell Line in Response to Ginkgo Biloba Extract: Induction of Antioxidant Response and the Golgi System, Free Radic Res. 2001 December;33(6):831-849.

We may also test combinations of plants for synergistic effects by using the mouse model for diabetic lesions, as described in Mastropaolo, et al., Synergy in Polymicrobial Infections in a Mouse Model of Type 2 Diabetes Infection and Immunity, September 2005, p. 6055-6063, Vol. 73, No. 9. Briefly, obese diabetic mouse strain BKS.Cg-m +/+ Leprdb/J are injected subcutaneously with mixed cultures containing *Escherichia coli Bacteroides fragilis*, and *Clostridium perfringens*. Progression of the infection (usually abscess formation) is monitored by examining mice for bacterial populations and numbers of white blood cells at 1, 8, and 22 days post-infection. Various plant ingredients and combinations thereof can be used to show a synergistic effect. Further, the model can be used to show synergy when the formulations of the invention are combined with existing pharmaceuticals, such as antibiotics.

What is claimed is:

1. A method of treating diabetic lesions comprising administering a composition comprising effective amounts of the following active ingredients: Eleutherococcus senticosus, Rhaponticum carthamoides, Panax ginseng, Panax quinquefolius, Pfaffia paniculada (Suma), Rhodiola rosea, Echinacea angustifolia, Echinacea purpurea, Ganoderma lucidum, Grifola frondosa, Hydrastis canadensis, Petiveria alliacea, Sutherlandia frutescens, Tabebuia avellanedae, Uncaria tomentosa, Angelica sinensis, Crataegus oxyacantha, Croton lechleri, Ginkgo biloba, Hydrocotyle asiatica, Ruscus aculeatus, Vaccinium myrtillus, to a patient in an amount sufficient to alleviate diabetic lesions.

2. A method of treating diabetic lesions comprising administering an effective amount of the composition of Table 1 to a patient sufficient to alleviate diabetic lesions.

* * * * *